US00PP25606P3

(12) United States Plant Patent
Bentley

(10) Patent No.: US PP25,606 P3
(45) Date of Patent: May 26, 2015

(54) ***SALVIA* PLANT NAMED 'EGGBEN008'**

(50) Latin Name: *Salvia gregii×microphylla*
Varietal Denomination: Eggben008

(71) Applicant: Howard Bentley, Wonga Park (AU)

(72) Inventor: Howard Bentley, Wonga Park (AU)

( * ) Notice: Subject to any disclaimer, the term of this patent is extended or adjusted under 35 U.S.C. 154(b) by 13 days.

(21) Appl. No.: 13/987,371

(22) Filed: Jul. 17, 2013

(65) Prior Publication Data

US 2015/0026855 P1 Jan. 22, 2015

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Anne Grunberg
(74) *Attorney, Agent, or Firm* — Cassandra Bright

(57) ABSTRACT

A new and distinct *Salvia* cultivar named 'EGGBEN008' is disclosed, characterized by a dense, bushy plant habit, strong peduncles, deep cerise colored flowers without a white eye. Flowers have a calyx flushed with dark anothocyanin. The new variety is a *Salvia*, normally produced as an outdoor garden or container plant.

2 Drawing Sheets

Latin name of the genus and species: *Salvia gregii×microphylla.*

Variety denomination: 'EGGBEN008'.

BACKGROUND OF THE INVENTION

The new *Salvia* cultivar is a product of a planned breeding program conducted by the inventor, Howard Bentley, in Wonga Park, Victoria, Australia. The objective of the breeding program was to produce new *Salvia* varieties with denser plant habits, strong garden performance, in a range of flower colors. The controlled pollination resulting in this new variety was made during March and April of 2007.

The parent variety is *Salvia gregii×microphylla* 'Eggben005', U.S. Plant Pat. No. 24,151. The parent variety was self-pollinated to produce an F2 generation of seed. This seed was collected, sown and grown outdoors under field conditions. The new variety was identified as a potentially interesting selection in October of 2009, at a research greenhouse in Wonga Park, Australia. Further observations and evaluations were made throughout 2010 and 2011.

Asexual reproduction of the new cultivar 'EGGBEN008' by vegetative cuttings was first performed during 2011, at a research greenhouse in Wonga Park, Australia. Subsequent propagation has shown that the unique features of this cultivar are stable and reproduced true to type on successive generations.

SUMMARY OF THE INVENTION

The cultivar 'EGGBEN008' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EGGBEN008' These characteristics in combination distinguish 'EGGBEN008' as a new and distinct *Salvia* cultivar:

1. Bushy plant habit.
2. Deep cerise flower color with no white eye.
3. Sturdy inflorescence.
4. Dense plant habit.
5. Dark anthocyanin coloration of calyx.

PARENT COMPARISON

Plants of the new cultivar 'EGGBEN008' are similar to plants of the parent, in most horticultural characteristics, however, plants of the new cultivar 'EGGBEN008' produce a darker colored flower, without the white eye found in the parent variety. Additionally, the new variety typically shows stronger anthocyanin coloration in the calyx.

COMMERCIAL COMPARISON

Plants of the new cultivar can be compared to the commercial variety *Salvia gregii* 'RFD-S018', U.S. Plant Pat. No. 14,699. The two *Salvia* varieties are very similar in most horticultural characteristics, however, the new variety produces deeper coloration in the calyx, a stronger and longer peduncle. Foliage differs as well; the new variety has more deeply incised foliage than 'RFD-S018'.

BRIEF DESCRIPTION OF THE PHOTOGRAPHS

Figure 1:
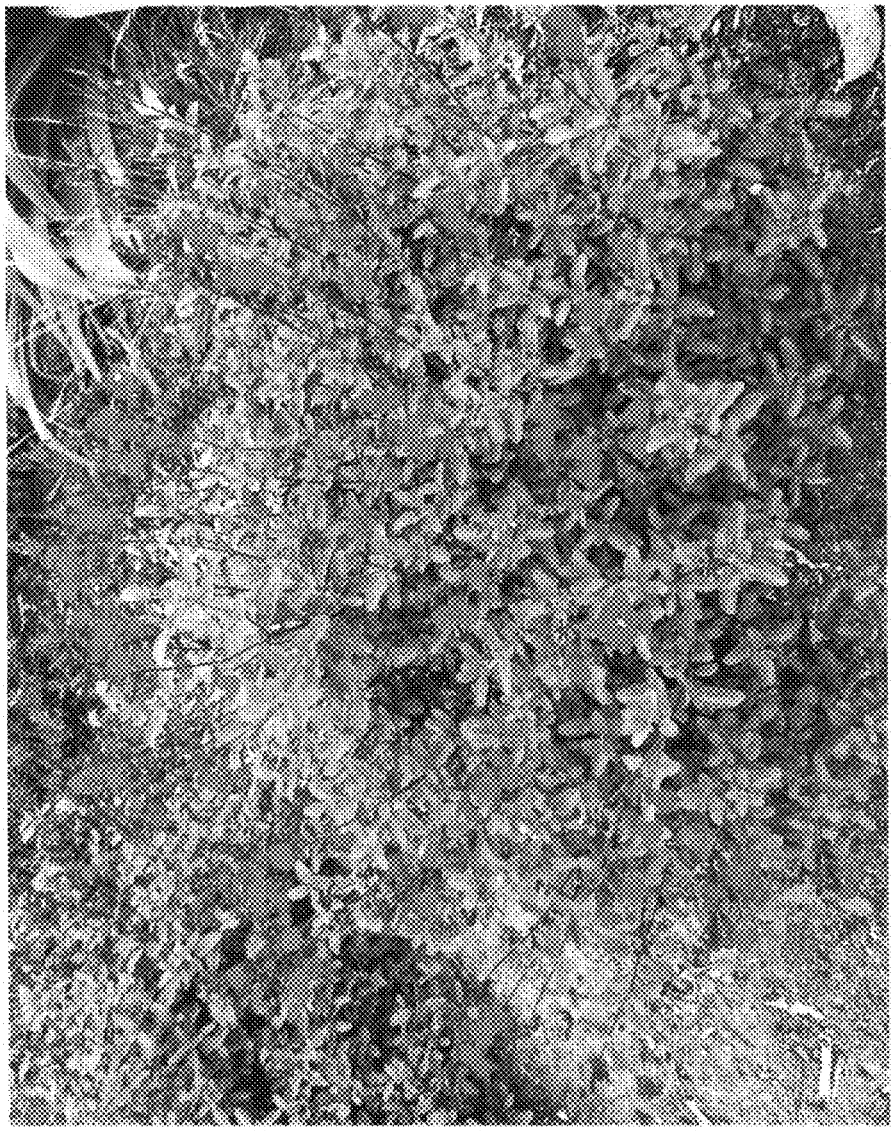

The accompanying photograph in FIG. 1 illustrates in full color a typical plant of 'EGGBEN008'.

Figure 2:
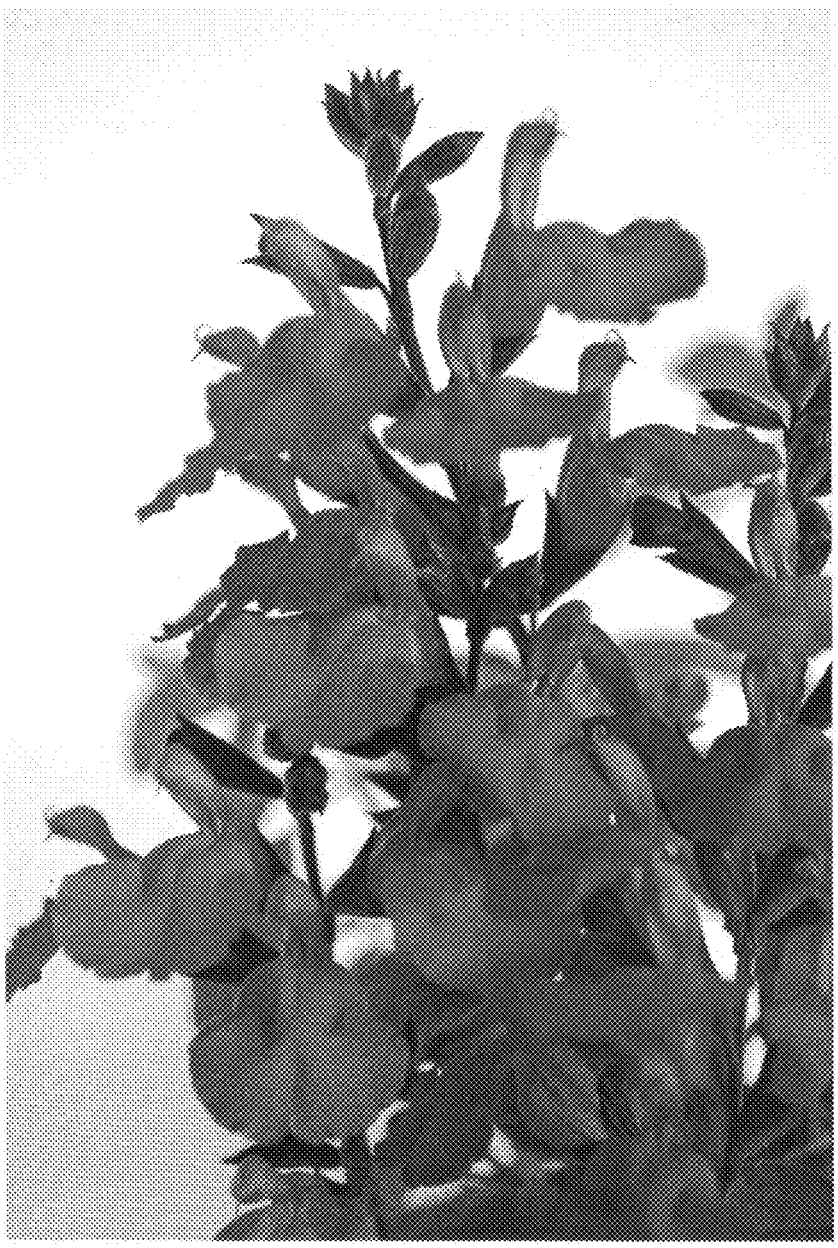

FIG. 2 illustrates in full color typical flowers of 'EGGBEN008'.

The plant was grown outdoors, in Wonga Park, Australia. Age of the plant photographed is approximately 50 weeks from an unrooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'EGGBEN008' plants grown outdoors in Wonga Park, Australia. The growing temperature ranged from approximately 5° C. to 35° C. Measurements and numerical values represent averages of typical plant types.

Botanical classification: *Salvia gregii×microphylla* 'EGGBEN008'.

PROPAGATION

Time to initiate roots: About 5-8 days at approximately 25° C.

Root description: Fine, densely fibrous.

Time to produce a rooted cutting: About 21 days at 25° C.

PLANT

Growth habit: Upright, bushy annual.

Height: Approximately 50 cm to top of foliage. Approximately 70 cm to top of flowering plane. Measured from soil level of pot.

Plant spread: Approximately 90 cm.

Growth rate: Rapid.

Branching characteristics: Free-branching, Approximately 8 to 10 primary branches.

Length of primary lateral branches: Approximately 45 cm.

Diameter of lateral branches: Approximately 0.35 cm.

Quantity of lateral branches: About 12 to 18.

Stem:

*Color*.—Near RHS Green 138A, flushed with Greyed-Purple 183B.

*Pubescence*.—Minute pubescence.

Internode length: Approximately 2.0 to 3.0 cm.

Age of plant described: Approximately 50 weeks from an unrooted cutting.

FOLIAGE

Leaf:

*Arrangement*.—Opposite.

*Quantity*.—Approximately 16 fully expanded per main branch.

*Average length*.—Approximately 5.2 cm., including petiole.

*Average width*.—Approximately 2.3 cm.

*Shape of blade*.—Obovate.

*Apex*.—Obtuse.

*Base*.—Obtuse to nearly truncate.

*Attachment*.—Stalked.

*Margin*.—Crenate.

*Texture of top surface*.—Matte, minute, coarse pubescence.

*Texture of bottom surface*.—Matte, minute, coarse pubescence.

*Color*.—Young foliage upper side: Near RHS Green 137A. Young foliage under side: Near RHS Green 137B. Mature foliage upper side: Near RHS Green 137A. Mature foliage under side: Near RHS Green 138A.

*Venation*.—Type: Pinnate. Venation color upper side: Near RHS Yellow-Green 144A. Venation color under side: Near RHS Green 143C.

*Petiole*.—Average Length: Approximately 1 cm. Diameter: Approximately 0.1 cm. Color: Near Green 143C.

FLOWER

Natural flowering season: Flowering from early Spring through late Summer.

Inflorescence type and habit: Flowers arranged in verticillasters on spikes.

Flower longevity on plant: Individual flowers last approximately 1 week on the plant. Each spike lasts approximately 7 weeks with flowers.

Quantity of flowers: About 8 to 12 buds and 6 to 10 fully opened flowers per spike, at one time. Mature plants have approximately 10 to 20 spikes.

Spike size:

*Diameter*.—Approximately 8 cm.

*Height*.—Approximately 12 cm.

Individual flowers:

Size:

*Diameter*.—Approximately 2.5 cm.

*Length*.—Approximately 3.0 cm.

*Persistence*.—Non-persistent.

*Fragrance*.—Moderate, typical *Salvia* scent.

Corolla:

*Petal arrangement*.—The corolla is sympetalous and typically bilabiate with 2 small, highly fused lobes forming an upper lip and 3 larger highly fused lobes forming a lower lip.

*Margin*.—Nearly entire, slightly scalloped.

*Tip shape*.—Upper lip tip retuse, lower lip tip rounded with scallops.

*Length*.—Upper lip Approximately 1.3 cm, lower lip Approximately 1.8 cm. Tube length Approximately 2.1 cm.

*Width*.—Upper lip Approximately 0.4 cm, lower lip Approximately 2.5 cm. Tube width Approximately 0.8 cm.

*Texture*.—Upper lip: Highly pubescent on exterior surface. Interior surface glabrous. Lower lip: Glabrous all surfaces.

Color:

*Upper lip*.—When opening: Inner surface: Background color Near RHS Red-Purple 71C. Outer surface: Background color Near RHS Red-Purple 70A. Fully opened: Inner surface: RHS Red-Purple 71B. Outer surface: RHS Red-Purple 70A. Fading: Inner surface: RHS Red-Purple 70B. Outer surface: RHS Red-Purple 70B.

Color:

*Lower lip*.—When opening: Inner surface: RHS Red-Purple 61A. Outer surface: RHS Red-Purple 61A. Fully opened: Inner surface: RHS Red-Purple 61A. Outer surface: RHS Red-Purple 61A. Fading: Inner surface: Near RHS Red-Purple 64B. Outer surface: Near RHS Red-Purple 64B.

Color:

*Tube*.—When opening: Inner surface: Near RHS Red-Purple 64A. Outer surface: Near RHS Red-Purple 64C. Fully opened: Inner surface: Near RHS Red-Purple 64A. Outer surface: Near RHS Red-Purple 64C. Fading: Inner surface: Near RHS Red-Purple 64A. Outer surface: Near RHS Red-Purple 64C.

Bud:
*Shape*.—Ovoid.
*Length*.—Approximately 1.4 cm.
*Diameter*.—Approximately 0.8 cm.
*Color*.—Near RHS Red-Purple 71B.

Calyx:
*Length*.—Approximately 1.6 cm.
*Diameter*.—Approximately 1 cm.
*Shape*.—Tubular.

Sepals:
*Shape*.—Quantity per flower: 3, fused to form a tube.
*Unfused apex*.—Length: Approximately 0.7 cm. Width: Approximately 0.5 cm. Margin: Entire. Apex: Acute. Texture: Pubescent. Color: Immature: Near RHS Yellow-Green 147A, flushed Greyed-Purple 187A. Mature: Near RHS Yellow-Green 147A, flushed Red-Purple 59A.

Peduncle:
*Length*.—Average 7.7 cm.
*Diameter*.—0.3 cm.
*Color*.—Near RHS Green 137A, flush near Greyed-Purple N187A.
*Orientation*.—Upright, straight.
*Strength*.—Strong.
*Texture*.—Pubescent.

Pedicels:
*Length*.—Average 0.2 cm.
*Diameter*.—0.1 cm.
*Color*.—Near RHS Greyed-Purple N187A.
*Orientation*.—Straight, approximately 45 degree angle from attachment.
*Strength*.—Flexible.
*Texture*.—Pubescent.

REPRODUCTIVE ORGANS

Stamens:
*Number*.—2.
*Filament length*.—Approximately 1.4, approximately 0.6 cm of length fused to petal.
*Filament color*.—Near RHS White N155B.

Anthers:
*Shape*.—Very narrowly elliptic.
*Length*.—Approximately 3 mm.
*Color*.—Near RHS Greyed-Yellow 161B.
*Pollen*.—Scant colored near Yellow 13B.

Pistil:
*Number*.—1.
*Length*.—Approximately 2.9 cm.
*Color*.—Near RHS White N155B.
*Stigma*.—Shape: Linear, curled. Color: Near RHS Red-Purple 59A. Ovary color: Near RHS Green-Yellow 1B.

OTHER CHARACTERISTICS

Seeds and fruits: Not observed to date.

Disease/pest resistance: Neither resistance nor susceptibility to pathogens and pests common to *Salvia* have been observed.

Temperature tolerance: The new variety tolerates temperatures between 5 to 35° C.

What is claimed is:

1. A new and distinct cultivar of *Salvia* plant named 'EGGBEN008' as herein illustrated and described.

* * * * *